United States Patent [19]
Shah et al.

[11] Patent Number: 6,028,212
[45] Date of Patent: Feb. 22, 2000

[54] SOLID VINYL ETHER TERMINATED URETHANE CURING AGENT

[75] Inventors: Navin B. Shah; Andrew T. Daly, both of Sinking Spring, Pa.

[73] Assignee: Morton International, Inc., Chicago, Ill.

[21] Appl. No.: 08/991,125

[22] Filed: Dec. 16, 1997

[51] Int. Cl.[7] ...................... C07C 269/02; C07C 271/24; C07D 251/34; C08G 18/04
[52] U.S. Cl. ............................ 560/115; 526/301; 528/49; 528/59; 528/73; 528/75; 544/193; 544/222; 560/158
[58] Field of Search .................................. 528/49, 59, 73, 528/75; 544/193, 222; 560/115, 158; 526/301

[56] References Cited

U.S. PATENT DOCUMENTS

| | | | |
|---|---|---|---|
| 4,749,807 | 6/1988 | Lapin et al. | 560/91 |
| 4,751,273 | 6/1988 | Lapin et al. | 525/455 |
| 4,775,732 | 10/1988 | Lapin | 528/49 |
| 4,956,198 | 9/1990 | Shama et al. | 427/54.1 |
| 4,996,282 | 2/1991 | Noren et al. | 528/75 |
| 5,019,636 | 5/1991 | Lapin et al. | 526/301 |
| 5,139,872 | 8/1992 | Lapin et al. | 428/375 |
| 5,200,490 | 4/1993 | Jaeger et al. | 528/49 |
| 5,437,964 | 8/1995 | Lapin et al. | 430/280 |
| 5,922,473 | 7/1999 | Muthiah et al. | 428/481 |

FOREIGN PATENT DOCUMENTS

| | | |
|---|---|---|
| 0636669 | 2/1995 | European Pat. Off. . |
| 0 844 286 | 12/1997 | European Pat. Off. . |

OTHER PUBLICATIONS

CDC Alert, *Preventing Asthma and Death from Diisocyarate Exposure*, DHHS (NIOSH) Publication No. 96–111 (1996).
Myer, H.Everett, et al., *A Survey of Airborne HDI, HDI-ased Polyisocyanate and Solvent Concentrations in the Manufacture of Polyurethane Coatings*, Am. Ind. Hyg. Assoc. J. 54 (11): 663–670 (1993).

*Primary Examiner*—Rabon Sergent
*Attorney, Agent, or Firm*—Steven C. Benjamin; Gerald K. White

[57] ABSTRACT

Solid vinyl ether terminated curing agents for powder coatings can be prepared by reacting an aliphatic diisocyanate with a polyol and then with a hydroxy vinyl ether, or by reacting an aliphatic polyisocyanate with a hydroxy vinyl ether. Powder coatings based on the so prepared curing agents are extremely useful for coating heat sensitive substrates by exposure to ultraviolet light, heat, or both.

21 Claims, No Drawings

SOLID VINYL ETHER TERMINATED URETHANE CURING AGENT

FIELD OF THE INVENTION

This invention relates to vinyl ether terminated urethane curing agents. More particularly, this invention relates to vinyl ether terminated urethane curing agents that are derived from relatively safe, non-hazardous materials, and that are non-crystalline solids at room temperature to enable use in powder coatings.

BACKGROUND OF THE INVENTION

Vinyl ether terminated urethane resins are extremely reactive prepolymers which are known to undergo rapid polymerization when exposed to radiation. These compounds are particularly useful as curing agents in applications which require high speed curing of a resin formulation, such as in radiation curable coatings.

One disadvantage attendant to the use of such vinyl ether functionalized urethanes is that their commercial availability is relatively limited. In general, the available prepolymers constitute liquid or semi-solid (with extremely low Tg° C.) materials. U.S. Pat. No. 4,751,273 (Lapin, et al.) provides specific examples of such liquid and semi-solid vinyl ether terminated urethane resins.

These curing agents, though extremely useful in liquid radiation curable coatings, have only limited use in powder coatings. Typically, because of their liquid or semi-solid state, they cannot be used beyond a few percent (<5%) in powder coatings. Greater amounts typically cause the powder to block or sinter in storage, which renders the powder unsprayable during electrostatic coating operations.

Solid vinyl ether terminated urethane curing agents which are more conducive for use in radiation curable powder coatings have been proposed. For example, EP-A-0 636 669 (DSM, N.V.) provides one example of a crystalline vinyl ether functionalized urethane curing agent that remains a solid at room temperature (melt range of 90–108° C.). This curing agent arises from the reaction of hydroxybutyl vinyl ether (HBVE) with hexamethylene diisocyanate (HDI) monomer in a 1:1 (stoichiometric) mole ratio of hydroxy to isocyanate groups. The reaction product is a short chain crystalline urethane oligomer (HBVE-HDI-HBVE).

One disadvantage with the use of such a crystalline curing agent in powder coatings is that it makes manufacture of the powders extremely troublesome. Powders based on crystalline materials take longer to recrystallize after melt extrusion, making subsequent grinding and handling very messy and difficult.

Another disadvantage with the use of this curing agent is that monomeric HDI is known to be unsafe to handle because of its high toxicity. Thus, the presence of residual (unreacted) monomeric HDI in the curing agent will expose the end user to serious health hazards. For instance, HDI monomer has been known to cause skin sensitization, which can lead to serious respiratory disease in workers, including asthma and permanent decrease in lung functions. Furthermore, HDI monomer readily becomes airborne because of its high vapor pressure at room temperature which, in turn, increases the risk of inhalation of its vapors or mists.

It would be desirable to provide a vinyl ether terminated urethane curing agent that is solid at room temperature, is easier to melt process, is much safer to handle, and is effective in curing powder coatings.

SUMMARY OF THE INVENTION

It is an object of this invention, therefore, to provide a vinyl ether terminated urethane curing agent which does not suffer from the foregoing drawbacks.

It is another object of this invention to provide a vinyl ether terminated urethane curing agent that is derived from safer and less hazardous monomers.

Still another object of this invention is to provide a vinyl ether terminated urethane curing agent that remains a solid at room temperature.

And yet another object of this invention is to provide a method for preparing vinyl ether terminated urethane curing agents of the aforesaid character.

Another object of this invention is to provide a vinyl ether terminated urethane curing agent that can be effectively incorporated into powder coatings without degrading the shelf stability and electrostatic sprayability of the powder.

Still another object of this invention is to provide a vinyl ether terminated urethane curing agent that is a non-crystalline material, making powder coatings based on the same easier to melt process and handle during powder manufacture.

And still another object of this invention is to provide a vinyl ether terminated urethane curing agent that is extremely useful in curing powder coatings, particularly powder coatings that are curable by exposure to radiation, heat, or both, and especially those that can be used to coat heat sensitive substrates, such as wood and plastic, without causing permanent thermal damage to the substrate during curing.

The various objects, features and advantages of this invention will become more apparent from the following description and appended claims.

DETAILED DESCRIPTION OF THE PREFERRED EMBODIMENTS OF THE INVENTION

This invention provides vinyl ether terminated urethane prepolymers that are prepared from safer and less hazardous materials, and that are non-crystalline solids at room temperature to enable them to be extremely useful as curing agents in powder coatings. This invention also provides a method for the preparation of the same.

Broadly stated, the desired vinyl ether terminated urethane curing agents of this invention can be prepared by reacting an aliphatic diisocyanate monomer with a polyol, and then reacting the product obtained with a hydroxy vinyl ether, or by reacting an aliphatic polyisocyanate with a hydroxy vinyl ether. In this invention, the reactants are chosen particularly from materials which are relatively safe and less hazardous to handle. Furthermore, the reaction product which is obtained by either of the above preparation methods will comprise vinyl ether terminated urethane prepolymers that are non-crystalline solids at room temperature or higher.

In the first embodiment of the invention, the desired product is prepared by the two-step reaction sequence wherein a non-crystallizing aliphatic diisocyanate monomer (with relatively low vapor pressure) is first reacted with a crystallizing or non-crystallizing polyol, the resulting material being an adduct of the diisocyanate with the polyol, and then the adduct so obtained is further reacted with a hydroxy vinyl ether to end-cap the adduct with a hydroxy vinyl ether, the resulting material being a non-crystalline solid vinyl ether terminated urethane prepolymer.

The first reaction between the aliphatic diisocyanate monomer and the polyol can be viewed as an addition reaction wherein an adduct of diisocyanate with a polyol is formed. The reaction conditions will be chosen so as to form an isocyanate terminated urethane oligomer to the virtual exclusion of alcohol terminated polymeric materials.

The aliphatic diisocyanate monomers which may be employed in the first reaction include those selected from materials that are non-crystallizing, possess a vapor pressure less than that of monomeric hexamethylene diisocyanate (HDI) at room temperature (i.e., less than 0.011 mm Hg at 25° C.), and that preferably contain isocyanates with different reactivities. The inventors have thus far identified only one material which meets the above criterion, which is isophorone diisocyanate (IPDI). Thus, in the preferred embodiment of the invention, isophorone diisocyanate (vapor pressure 0.00048 mm Hg at 25° C.) is employed in the first reaction.

The polyols which may be subjected to the first reaction include those selected from crystallizing or non-crystallizing polyols, although non-crystallizing polyols are preferred. Examples of suitable diols useful herein include ethylene glycol, diethylene glycol, triethylene glycol, 1,2-propylene glycol, 1,3-propylene glycol, 1,3-butylethyl propanediol, neopentyl glycol (2,2'-dimethyl-1,3-propanediol), 2-butyl-2-ethyl-1,3-propanediol (BEPD), 2-methyl-1,3-propanediol (MP diol), 1,2-butylene glycol, 1,3-butylene glycol, 1,4-butylene glycol, 1, 3-isobutanediol, 1,2-isobutanediol, 2,3-butanediol, 2-butenediol(1,4), 2,2,4-trimethyl-1,3-pentanediol, 1,2-cyclopentanediol, 1,3-cyclopentanediol, 1,4-cyclopentanediol, 1,6-hexanediol, 1,4-dimethoxy cylcohexane, 1,2-cyclohexanediol, 1,3-cyclohexanediol, 1,4-cyclohexanediol, 1,4-cyclohexanedimethanol, 4,4'-methylene-bis(cyclohexanol), 4,4'-isopropylidene-bis (cyclohexanol), (hydrogenated bisphenol A) 1,4-bis (hydroxymethyl)cyclohexane, 1,3-bis(hydroxyethyl) cyclohexane, 1,3-bis(hydroxypropyl) cyclohexane, 1,3-bis (hydroxyisopropyl) cyclohexane, dodecanediol, xylene glycol, 4,4'-isopropylidene diphenol (bisphenol A), bisphenol A/propylene oxide adducts, hydroquinone/propylene oxide adducts, and hydroquinone/ethylene oxide adducts. In the preferred embodiment of the invention, neopentyl glycol (NPG) is employed in the first reaction.

The reaction conditions which may be employed in the first reaction will include temperatures in the range of about 75 to 100° C. Care must be taken to control the urethane reaction exotherm. The reaction is also usually performed in a moisture-free atmosphere, such as in a nitrogen atmosphere. It is also preferred that the reaction is carried out in the presence of a catalyst. A particularly preferred catalyst is one that contains tin, for example, dibutyltin dilaurate. In the reaction, a stoichiometric excess amount of the aliphatic diisocyanate is employed. Generally, the reactants are present in about a 2:1 to 2:1.5 mole ratio of isocyanate to hydroxy groups. But, in the preferred embodiment of the invention, the reactants are present in about a 2:1 mole ratio of isocyanate to hydroxy groups.

The first reaction may be illustrated by the following equation in which the preferred reactants are reacted in the preferred molar equivalent proportions:

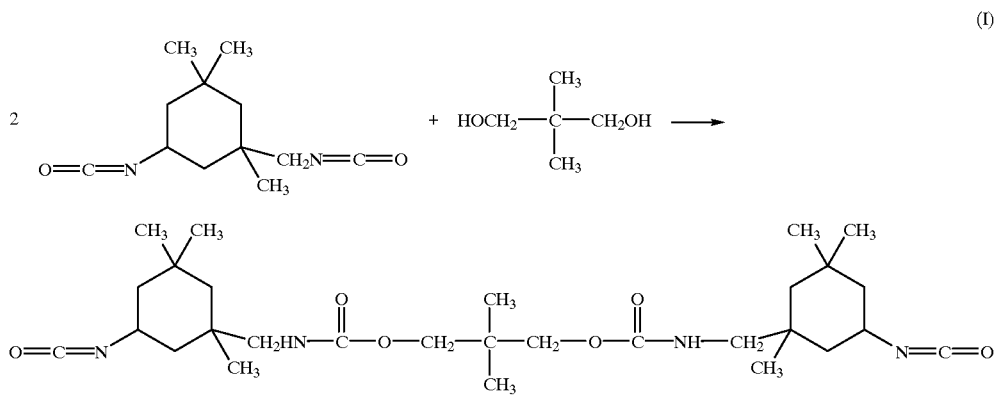

(I)

The product obtained by the first reaction, which will comprise the isocyanate terminated or end-capped urethane oligomer, will subsequently be reacted in the second reaction with a hydroxy vinyl ether to end-cap the product with vinyl ether groups and form the desired non-crystalline solid vinyl ether terminated urethane prepolymer.

The hydroxy vinyl ethers which may be employed in making the desired product include those prepared by any of the methods well known to those of ordinary skill in the art. The hydroxy vinyl ethers are usually prepared by the reaction of acetylene with polyols at elevated temperatures in the presence of a basic catalyst. Examples of hydroxy vinyl ethers which are commercially available and useful herein include hydroxybutyl vinyl ether and hydroxyethyl vinyl ether. It is understood that other hydroxy vinyl ethers may be used, for example, those having the general formula $CH_2=CH-O-R-OH$ where R is selected from the group of alkyl, aryl, alkaryl, aralkyl, cycloalkyl, and alkyl oxide radicals, although n-butyl is preferred. Thus, in the preferred embodiment of the invention, hydroxybutyl vinyl ether (HBVE), particularly 4-hydroxybutyl vinyl ether, is employed in the second reaction.

The reaction conditions which may be employed in the second reaction are generally the same as those of the first reaction. Usually, this reaction will immediately follow the completion of first reaction in the same reaction vessel. Care must be taken here as well to control the exotherm. In the preferred embodiment of the invention, the reactants are employed in stoichiometric equivalent amounts. Thus, the reactants are present in about a 1:1 mole ratio of isocyanate to hydroxy groups to ensure complete polymerization.

The second reaction may be illustrated by the following equation in which the preferred reactants are reacted in the preferred molar equivalent proportions:

handle and presents much lower health risks to the end user, since the monomeric diisocyanate material is particularly selected for its relatively low vapor pressure at room temperature. The vinyl ether terminated urethane resins which are obtained are, therefore, relatively safe, non-crystalline, solids at room temperature that are particularly suited for curing powder coatings.

In the second embodiment of the invention, the desired product is prepared by a one-step end-cap reaction sequence wherein a non-crystallizing aliphatic polyisocyanate (with relatively low vapor pressure) is reacted with a hydroxy vinyl ether.

The aliphatic polyisocyanates which may be employed in the one-step reaction are selected from materials that are non-crystallizing and possess a lower vapor pressure than monomeric HDI at room temperature. Examples of aliphatic polyisocyanate that meet the above criterion include the

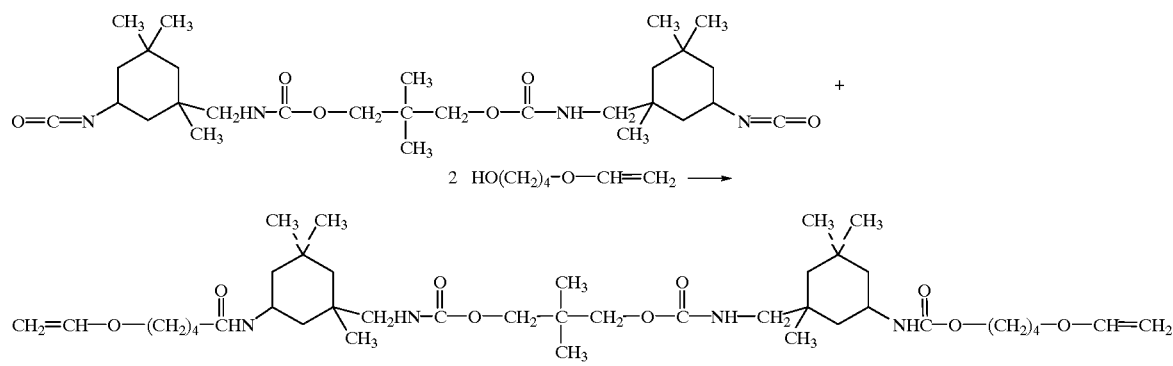

The product obtained by the second reaction will be the desired non-crystalline solid vinyl ether terminated urethane prepolymer final product which contains more than one diisocyanate in the polymer chain. The product may be semi-crystalline or amorphous, but more likely a non-crystallizing, amorphous prepolymer is formed.

As can be seen from equations I and II above, the first reaction with the polyol serves to chain extend the final prepolymer product, since each available hydroxy group on the polyol will react with an isocyanate group and form a higher molecular weight isocyanate terminated reactant for the second reaction. This higher molecular isocyanate terminated urethane oligomer, in turn, serves to form the higher molecular weight vinyl ether terminated urethane product which can remain a solid at room temperature or above. The desired product generally has a Tg° C. higher than about 20° C., and typically in a range of from about 25° C. to about 45° C., or higher.

Furthermore, the use of the isocyanate terminated urethane oligomer as a reactant in the second reaction, instead of a monomeric diisocyanate, reduces the amount of residual diisocyanate monomer contained in the final product. While it is still likely that the reaction product obtained will contain a certain amount of residual (unreacted) aliphatic diisocyanate monomer, the curing agent is still relatively safer to functionalized polymers derived from IPDI, such as the isocyanurates and uretdiones. In the preferred embodiment of the invention, the isophorone diisocyanate isocyanurate (IPDI trimer) is employed in the reaction.

The hydroxy vinyl ethers which may be employed in making the desired product of the second embodiment include those mentioned above.

The reaction conditions which may be employed in the one-step reaction will include temperatures not to exceed about 110° C. Care must be taken to control the reaction exotherm as well. The reaction is also usually performed in a moisture free atmosphere, such as in a nitrogen atmosphere. It is preferred that the reaction is carried out in the presence of a catalyst such as an organotin catalyst, for example, dibutyltin dilaurate. In the reaction, a stoichiometric equivalent amount of the reactants is employed. Thus, the reactants are present in a 1:1 mole ratio of isocyanate to hydroxy groups to ensure complete polymerization.

The one-step reaction may be illustrated by the following equation in which the preferred reactants are reacted in the preferred molar equivalent proportions:

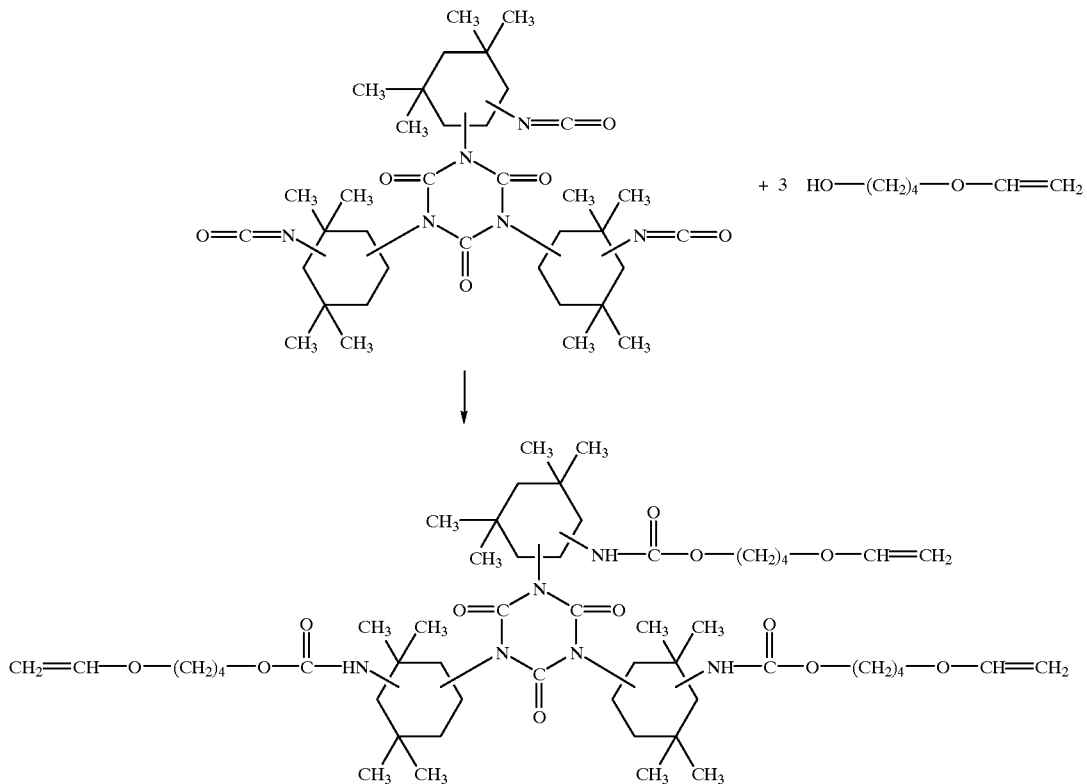

(III)

The product obtained by this reaction will be the desired non-crystalline solid vinyl ether terminated urethane prepolymer final product. This prepolymer may be semi-crystalline or amorphous, but more likely an amorphous prepolymer is formed.

The use of a polyisocyanate presents even lower health risks to the end user, since its vapor pressure is lower than its monomeric counterpart. The vinyl ether terminated urethane resins which are obtained are, therefore, relatively safer as well as non-crystalline, solids at room temperature that are particularly suited for curing powder coatings. The desired product generally has a Tg° C. higher than about 20° C., and typically in the range of from about 30° F. to about 50° C., or higher.

Non-sintering clear or pigmented powder coatings based on the aforesaid curing agents of this invention can be easily prepared in a conventional melt extrusion and grinding process. These powders may be formulated to cure by any method known in the art. For instance, the powder coatings may comprise film-forming resins which are crosslinkable with the solid vinyl ether urethane curing agents when exposed to heat (e.g., infrared or convection), radiation (e.g., electron beam or ultraviolet), or both, depending upon the type of cure initiator contained in the powder formulation. The crosslinkable resins particularly useful herewith are those based on unsaturated polymers, such as unsaturated polyesters and unsaturated poly(meth)acrylates.

Powder coatings based on the curing agents of this invention that include both a heat (e.g., peroxide initiator) and radiation (e.g., photoinitiator) curing aspect have been found especially suited for coating heat sensitive substrates, since they can be fully cured throughout at extraordinarily low temperatures so as to not cause thermal damage to the substrate.

Heat sensitive substrates coated with such powder coatings normally include hardwood, laminated bamboo, wood composites, such as particle board, electrically conductive particle board, fiber board, medium density fiberboard, masonite board, and other substrates that contain a significant amount of wood, all of which usually char, warp, outgas, or otherwise permanently degrade when coated and cured with traditional heat curable powders, and also plastics, such as ABS, PPO, SMC, polyolefins, acrylics, nylons, and other copolymers which usually will warp or outgas when coated and heat cured with traditional heat curable powders, as well as paper, cardboard, and composites and components with a heat sensitive aspect, and the like. Heat resistant substrates can be coated as well with such powders, including steel or other alloys in the form of sheet metal, rebars, pipelines, cold coil springs, and steel strapping, as well as glass, ceramic, such as ceramic tiles, carbon, graphite, and the like.

Moreover, powder coatings which employ the curing agents of this invention surprisingly exhibit improved flexibility and adhesion to the substrate after curing. It is believed that the polymeric nature of the curing agent serves to provide this advantageous effect.

This invention will be further clarified by a consideration of the following non-limiting examples which are intended to be purely exemplary of the invention.

EXAMPLE 1

Preparation of Solid Vinyl Ether Terminated Urethane Prepolymer

The following ingredients were reacted in the given proportions using a two-step reaction method (described in detail below) to form the solid vinyl ether terminated urethane prepolymer of this example.

| Ingredients | Wt. in grams | Molar Equivalents |
|---|---|---|
| Isophorone Diisocyanate (IPDI) | 222.0 | 2.0 equivalents |
| Neopentyl Glycol (NPG) | 52.0 | 1.0 equivalent |
| 4-Hydroxybutyl Vinyl Ether (HBVE) | 116.0 | 1.0 equivalent |
| Dibutyltin Dilaurate Catalyst | 0.012–0.015 wt. % | |

IPDI was charged in a 0.5 L reaction kettle, fitted with a stirrer, addition funnel, thermocouple controller, and nitrogen sparge inlet. Heating and stirring was started with nitrogen flow at the rate of 30–50 mL/min in the presence of tin catalyst. When the temperature reached 75° C., a portion of NPG (~25 wt. %) was added into the kettle. A strong exotherm took place indicating the onset of the urethane reaction. Care was taken to control the exotherm below 100° C. After the exotherm subsided, the second, third, and fourth portions of NPG were added over several hours while controlling the exotherm after each addition. The adduct had a free isocyanate content (% NCO) of 15.6% (15.3% theoretical). At this point, HBVE was added slowly through the addition funnel at the rate of 3–5 mL/min. During addition, a strong exothermic reaction took place. Care was taken to prevent the exotherm from exceeding 100° C. After addition was completed, mixing was continued until the free % NCO was below 0.3%. Finally the resin was discharged, cooled, ground, and then packaged. The product recovered comprised a non-crystallizing, amorphous material which was solid at room temperature and had a Tg° C. of about 25° C. and a molecular weight of 800 g/mol (theoretical).

EXAMPLE 2

Preparation of Dual Cure Powder Coating

The following ingredients were blended together in the given manner to form a pigmented powder coating that is curable by exposure to combined heat and UV radiation, and which has been found particularly suited for coating heat sensitive substrates.

| Ingredients | Phr |
|---|---|
| DRY BLEND UNTIL HOMOGENEOUS | |
| XP 3125 Unsaturated Polyester[1] | 80.0 |
| Vinyl Ether Curing Agent (Example 1) | 20.0 |
| Lucerin TPO Photoinitiator[2] | 2.0 |
| Irgacure 184 Photoinitiator[3] | 1.0 |
| Lupersol 231XL Peroxide Initiator[4] | 2.0 |
| Resiflow P-67 Acrylic Flow Aid[5] | 2.0 |
| TiPure R-902 Titanium Dioxide[6] | 25.0 |
| MELT BLEND IN EXTRUDER AT 180° F. | |
| COOL EXTRUDATE AND BREAK INTO CHIPS | |
| CHARGE TO MILL AND GRIND TO POWDER | |
| SCREEN TO –140 MESH | |

[1]XP 3125 Unsaturated Polyester is a solid, acid-functional, semi-crystalline, film-forming unsaturated polyester resin based on fumaric acid, terephthalic acid, and 1,6-hexanediol, sold by DSM Resins.
[2]Lucerin TPO Photoinitiator is a photoinitiator based on 2,4,6-trimethylbenzoyldiphenyl phosphine oxide, sold by BASF.
[3]Irgacure 184 Photoinitiator is an aryl ketone based on 1-hydroxycyclohexyl phenyl ketone, sold by Ciba Additives.
[4]Lupersol 231XL Peroxide Initiator is a peroxy ketal thermal inititaor based on 1,1-bis(t-butylperoxy)3,3,5-trimethylcyclohexane, sold by Elf Atochem.
[5]Resiflow P-67 is an acrylic flow aid sold by Estron Chemical.
[6]TiPure R-902 is a white titanium dioxide pigment, sold by Du Pont.

The powder coating was electrostatically sprayed with a triboelectric gun on ½" medium density fiber board (MDF) which had been preheated with quartz infrared (IR) lamps to about 200–250° F. The coated board was post heated with quartz IR lamps at about 400° F. for about 40 sec. to melt and flow the powder into a molten film and initiate the thermal cure. Immediately after flow out, the molten film was passed under two 600 watt V/H ultraviolet (UV) lamps at 20 ft./min. for about a total of 1 sec. to initiate UV cure. The cured powder coating exhibited the following properties on the MDF.

| Tests | Properties |
|---|---|
| MEK Rubs (50 Double Rubs) | No Effect |
| Cross Hatch Adhesion | 3B |
| Pencil Hardness Mar | HB |
| Gloss, 20°/60° | 38/86 |

EXAMPLE 3

Preparation of Solid Vinyl Ether Terminated Urethane Prepolymer

The following ingredients were reacted in the given proportions using a one-step reaction method (described in detail below) to form the solid vinyl ether terminated urethane prepolymer of this example.

| Ingredients | Wt. in grams | Molar Equivalents |
|---|---|---|
| IPDI Trimer T-1890[1] | 116.0 | 1.0 equivalent |
| HBVE | 116.0 | 1.0 equivalent |
| Dibutyltin Dilaurate Catalyst | 0.02 wt. % | |

[1]IPDI Trimer T-1890 is an isophorone diisocyanate trimer sold by Hüls.

HBVE was charged in a 0.5 L reaction kettle, fitted with a stirrer, addition funnel, thermocouple controller, and nitrogen sparge inlet. IPDI Trimer was added slowly with gentle stirring. After addition, stirring was continued with moderate heat applied (maximum temperature not to exceed 60° C.) until all IPDI Trimer had dissolved. After dissolution, the temperature was raised slowly to 100° C. The reaction mix was then allowed to react for 2–3 hours. At this time, the temperature was lowered to 70–75° C. and 0.075 gm. (0.02 wt. %) of dibutyltin dilaurate catalyst was added to the reaction mixture. Care was taken to control the exotherm below 110° C. Mixing was continued until the free % NCO was below 0.5%. Finally the resin was discharged, cooled, ground, and then packaged. The product recovered comprised a non-crystallizing, amorphous material which was solid at room temperature and had a Tg° C. in the range of about 30–35° C. and a Tm° C. of about 50–55° C.

From the foregoing it will be seen that this invention is one well adapted to attain all ends and objects hereinabove set forth together with the other advantages which are apparent and inherent. Since many possible variations may be made of the invention without departing from the scope thereof, the invention is not intended to be limited to the embodiments and examples disclosed, which are considered to be purely exemplary. Accordingly, reference should be made to the appended claims to assess the true spirit and scope of the invention, in which exclusive rights are claimed.

What is claimed is:

1. A non-crystalline solid vinyl ether terminated urethane prepolymer composition having the chemical formula:

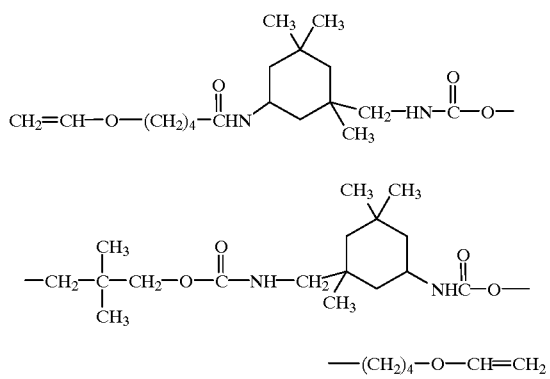

wherein said composition has a Tg° C. above 20° C.

2. The composition of claim 1 having an amorphous microstructure.

3. The composition of claim 1 having a Tg° C. in the range of from about 25 to about 45° C.

4. A non-crystalline solid vinyl ether terminated urethane prepolymer composition, comprising the reaction product of a hydroxy vinyl ether with an adduct obtained by a reaction of a non-crystallizing aliphatic diisocyanate monomer with a crystallizing or non-crystallizing polyol, wherein said aliphatic diisocyanate monomer comprises isophorone duisocyanate, and wherein said reaction product has a Tg° C. above 20° C.

5. The composition of claim 4, wherein said aliphatic diisocyanate has a vapor pressure less than 0.011 mm Hg at 25° C.

6. The composition of claim 4, wherein said hydroxy vinyl ether comprises hydroxybutyl vinyl ether.

7. The composition of claim 6, wherein said polyol is non-crystallizing polyol.

8. The composition of claim 7, wherein said polyol comprises neopentyl glycol.

9. The composition of claim 8, wherein said aliphatic diisocyanate, polyol, and hydroxy butyl vinyl ether are reacted in an amount of about 2:1:1 molar equivalents.

10. A method for the preparation of a non-crystalline solid vinyl ether terminated urethane prepolymer, comprising reacting about 2 molar equivalents of a non-crystallizing aliphatic diisocyanate monomer having a vapor pressure less than 0.011 mm Hg at 25° C. with about 1–1.5 molar equivalents of a crystallizing or non-crystallizing polyol, and then reacting the product obtained with about 1 molar equivalent of a hydroxy vinyl ether, and recovering the resultant non-crystalline solid vinyl ether terminated urethane prepolymer, wherein said aliophatic diisocvanate monomer comprises isophorone diisocyanate, and wherein the resultant product has a Tg° C. above 20° C.

11. The method of claim 10, wherein said polyol comprises non-crystallizing neopentyl glycol, and said hydroxy vinyl ether comprises hydroxybutyl vinyl ether.

12. A non-crystalline solid vinyl ether terminated urethane prepolymer composition having the chemical formula:

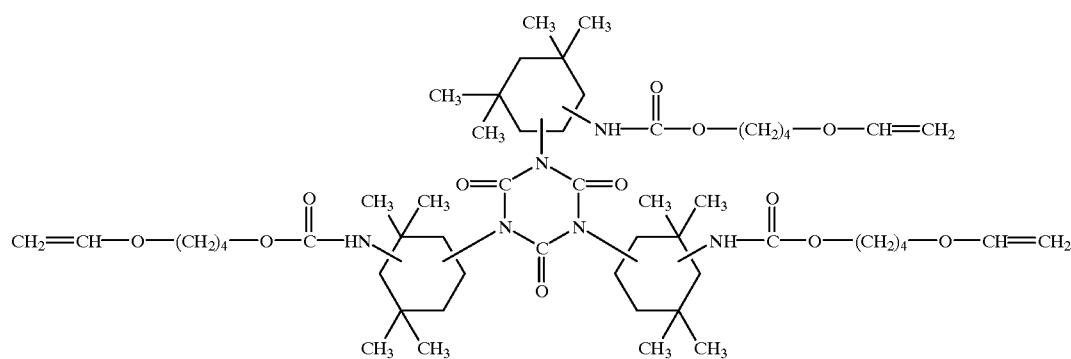

wherein said composition has a Tg° C. above 20° C.

13. The composition of claim 12 having an amorphous microstructure.

14. The composition of claim 12 having a Tg° C. in the range of from about 30 to about 50° C.

15. A non-crystalline solid vinyl ether terminated urethane prepolymer composition, comprising the reaction product of a hydroxy vinyl ether with a non-crystallizing aliphatic polyisocyanate, wherein said aliphatic polyisocyanate comprises a polyisocyanate derived from isophorone diisocyanate, and said reaction product has a Tg° C. above 20° C.

16. The composition of claim 15, wherein said aliphatic polyisocyanate has a vapor pressure less than 0.011 mm Hg at 25° C.

17. The composition of claim 15, wherein said aliphatic polyisocyanate comprises isophorone diisocyanate trimer.

18. The composition of claim 16, wherein said hydroxy vinyl ether comprises hydroxybutyl vinyl ether.

19. The composition of claim 18, wherein said aliphatic polyisocyanate and hydroxy butyl vinyl ether are reacted in stoichiometric equivalent amounts.

20. A method for the preparation of a non-crystalline solid vinyl ether terminated urethane prepolymer, comprising reacting stoichiometric equivalent amounts of a non-crystallizing aliphatic polyisocyanate having a vapor pressure less than 0.011 mm Hg at 25° C. with a hydroxy vinyl ether, and recovering the resultant non-crystalline solid vinyl ether terminated urethane prepolymer, wherein said aliphatic polyisocyanate comprises a polyisocyanate derived from isophorone diisocyanate, and wherein the resultant prepolymer has a Tg° C. above 20° C.

21. The method of claim 20, wherein said aliphatic polyisocyanate comprises isophorone diisocyanate trimer and said hydroxy vinyl ether comprises hydroxybutyl vinyl ether.

* * * * *